United States Patent
Chen et al.

(10) Patent No.: US 10,482,227 B2
(45) Date of Patent: Nov. 19, 2019

(54) ELECTROENCEPHALOGRAPHY (EEG) BASED AUTHENTICATION

(71) Applicant: International Business Machines Corporation, Armonk, NY (US)

(72) Inventors: Hao Chen, Beijing (CN); Ya Bin Dang, Beijing (CN); Qi Cheng Li, Beijing (CN); Shao Chun Li, Beijing (CN); Jie Ma, Beijing (CN); Lijun Mei, Beijing (CN); Jian Wang, Beijing (CN); Yipeng Yu, Beijing (CN); Xin Zhou, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 177 days.

(21) Appl. No.: 15/472,072

(22) Filed: Mar. 28, 2017

(65) Prior Publication Data

US 2018/0285540 A1 Oct. 4, 2018

(51) Int. Cl.
| | |
|---|---|
| *G06F 21/32* | (2013.01) |
| *G06F 3/01* | (2006.01) |
| *H04L 29/06* | (2006.01) |
| *A61B 5/0484* | (2006.01) |
| *A61B 5/117* | (2016.01) |

(52) U.S. Cl.
CPC .......... *G06F 21/32* (2013.01); *A61B 5/04842* (2013.01); *A61B 5/117* (2013.01); *G06F 3/015* (2013.01); *H04L 63/0861* (2013.01)

(58) Field of Classification Search
CPC ....... G06F 21/32; H04L 63/08; H04L 63/083; H04L 63/0861
See application file for complete search history.

(56) References Cited

U.S. PATENT DOCUMENTS

| | | | |
|---|---|---|---|
| 8,032,231 B1* | 10/2011 | Gilson | A61N 1/0534 607/116 |
| 8,818,498 B2* | 8/2014 | Terada | A61B 5/0478 600/383 |
| 9,020,586 B2* | 4/2015 | Yamada | G01R 33/4806 600/410 |
| 9,058,473 B2* | 6/2015 | Navratil | G06F 21/32 |
| 9,226,698 B2* | 1/2016 | Navratil | G06F 21/32 |

(Continued)

FOREIGN PATENT DOCUMENTS

| | | | |
|---|---|---|---|
| CN | 104868999 A | 8/2015 | |
| WO | WO-2016080366 A1 * | 5/2016 | ............. A61B 5/117 |
| WO | WO 2016/113717 A1 | 7/2016 | |

OTHER PUBLICATIONS

Su et al., "A Biometric-based Covert Warning System Using EEG", Published in 2012 5th IAPR International Conference on Biometrics (ICB) dated Mar. 29-Apr. 1, 2012. (Year: 2012).*

(Continued)

*Primary Examiner* — Linglan E Edwards
(74) *Attorney, Agent, or Firm* — Grant Johnson, Esq.; McGinn IP Law Group, PLLC

(57) ABSTRACT

An authentication method, system, and computer program product for decoding brain activity into a brain pattern sequence, applying brain dialog to interact with a user while the user is entering the brain pattern sequence, and matching the brain pattern sequence with a predetermined password to allow access to a system.

18 Claims, 9 Drawing Sheets

(56) References Cited

U.S. PATENT DOCUMENTS

| | | | | |
|---|---|---|---|---|
| 9,473,493 | B2* | 10/2016 | Jayaraman | A61B 5/04842 |
| 9,703,952 | B2* | 7/2017 | Almehmadi | G06F 21/552 |
| 9,779,575 | B1* | 10/2017 | Bagherzadeh | G07F 17/3262 |
| 9,876,791 | B2* | 1/2018 | Bae | H04L 63/0861 |
| 9,942,225 | B2* | 4/2018 | Navratil | G06F 21/32 |
| 10,044,712 | B2* | 8/2018 | Gordon | G02B 27/0172 |
| 2007/0250920 | A1* | 10/2007 | Lindsay | G06F 21/31 |
| | | | | 726/7 |
| 2011/0159467 | A1* | 6/2011 | Peot | A61B 3/113 |
| | | | | 434/157 |
| 2014/0228701 | A1* | 8/2014 | Chizeck | A61B 5/04012 |
| | | | | 600/544 |
| 2015/0216437 | A1* | 8/2015 | Mihajlovic | A61B 5/04012 |
| | | | | 600/545 |
| 2016/0004862 | A1* | 1/2016 | Almehmadi | G06F 21/552 |
| | | | | 726/25 |
| 2016/0021106 | A1 | 1/2016 | Navratil et al. | |
| 2016/0210407 | A1* | 7/2016 | Hwang | G06Q 50/22 |
| 2016/0282939 | A1* | 9/2016 | Sorensen | G06F 3/015 |
| 2016/0352727 | A1* | 12/2016 | Day | A61B 5/7221 |
| 2017/0185149 | A1* | 6/2017 | Oluwafemi | G06F 3/015 |
| 2017/0188933 | A1* | 7/2017 | Huggins | A61B 5/4088 |
| 2017/0325720 | A1* | 11/2017 | Hasegawa | A61B 5/117 |

OTHER PUBLICATIONS

Mel, et al. "The NIST Definition of Cloud Computing", Recommendations of the National Institute of Standards and Technology. Nov. 16, 2015.

Qiong Gui, et al. "Exploring EEG-based Biometrics for User Identification and Authentication" Department of Electrical and Computer Engineering, Dec. 2014.

* cited by examiner

ELECTROENCEPHALOGRAPHY (EEG) BASED AUTHENTICATION

BACKGROUND

The present invention relates generally to an authentication method, and more particularly, but not by way of limitation, to a system, method, and computer program product for using human brain signals to recognize individual identity by decoding brain activities into brain pattern sequences.

There are various biometric identification systems, such as fingerprint identification, hand geometry, palm vein authentication, retina scan, iris scan, face recognition, signature, voice analysis, etc. However, these methods have many shortcomings such as the passwords can be faked. Indeed, even if the owner dies, parts of his body can be used to obtain authentication. Thus, there is a need in the art to utilize human brain signals for identity recognition.

SUMMARY

In an exemplary embodiment, the present invention can provide a computer-implemented authentication method, the method including decoding brain activity into a brain pattern sequence, applying brain dialogue to interact with a user while the user is entering the brain pattern sequence, and matching the brain pattern sequence with a predetermined password to allow access to a system. One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which.

DETAILED DESCRIPTION

Figure 1:
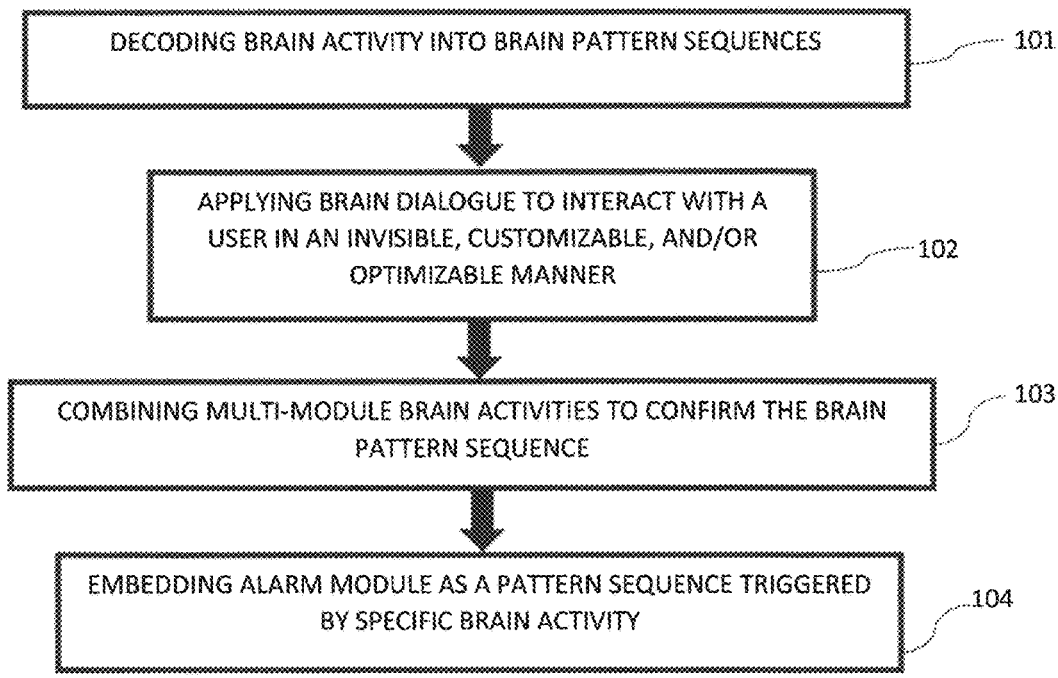
FIG. 1 exemplarily shows a high-level flow chart for an authentication method 100 according to an embodiment of the present invention.

The invention will now be described with reference to FIGS. 1-9, in which like reference numerals refer to like parts throughout. It is emphasized that, according to common practice, the various features of the drawings are not necessarily to scale. On the contrary, the dimensions of the various features can be arbitrarily expanded or reduced for clarity.

By way of introduction of the example depicted in FIG. 1, an embodiment of an authentication method 100 according to the present invention can include various steps for authenticating a user to a system (e.g., via a password or the like).

Figure 7:
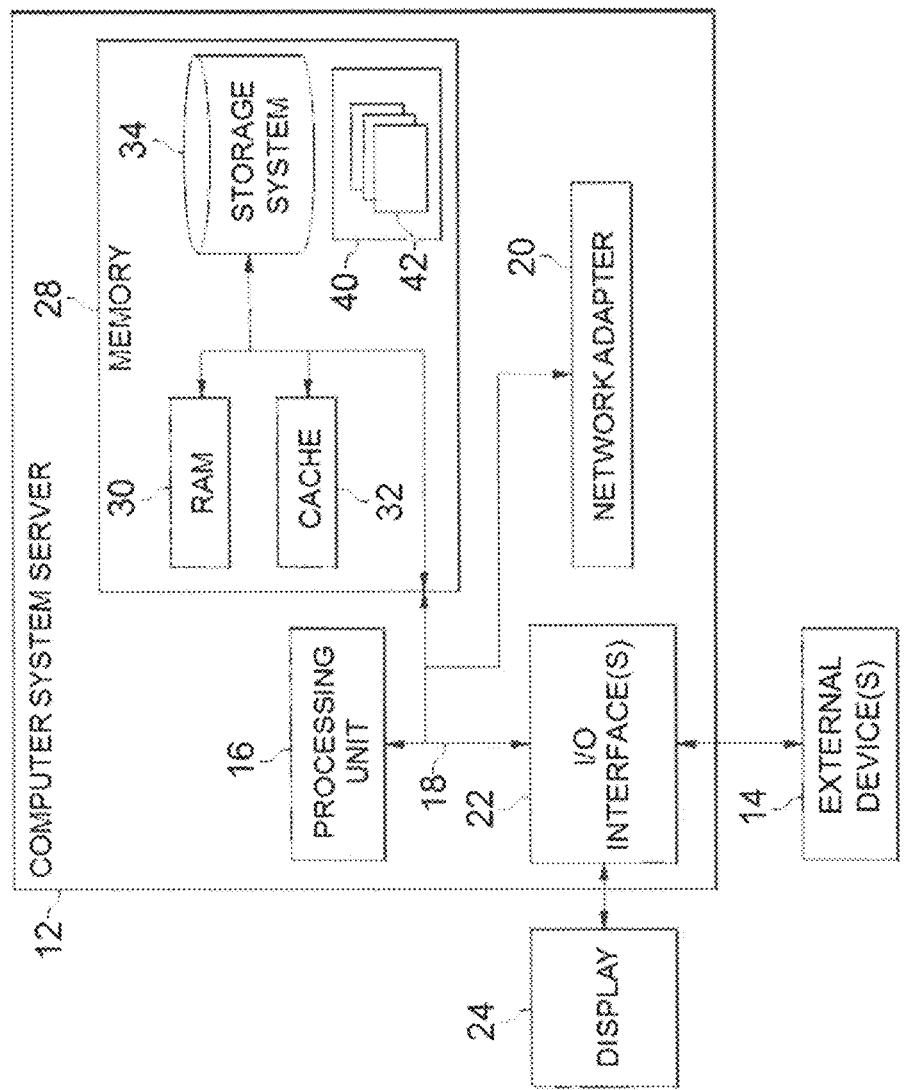
FIG. 7 depicts a cloud-computing node 10 according to an embodiment of the present invention.

By way of introduction of the example depicted in FIG. 7, one or more computers of a computer system 12 according to an embodiment of the present invention can include a memory 28 having instructions stored in a storage system to perform the steps of FIG. 1.

Although one or more embodiments may be implemented in a cloud environment 50 (see e.g., FIG. 8), it is nonetheless understood that the present invention can be implemented outside of the cloud environment.

Figure 6:
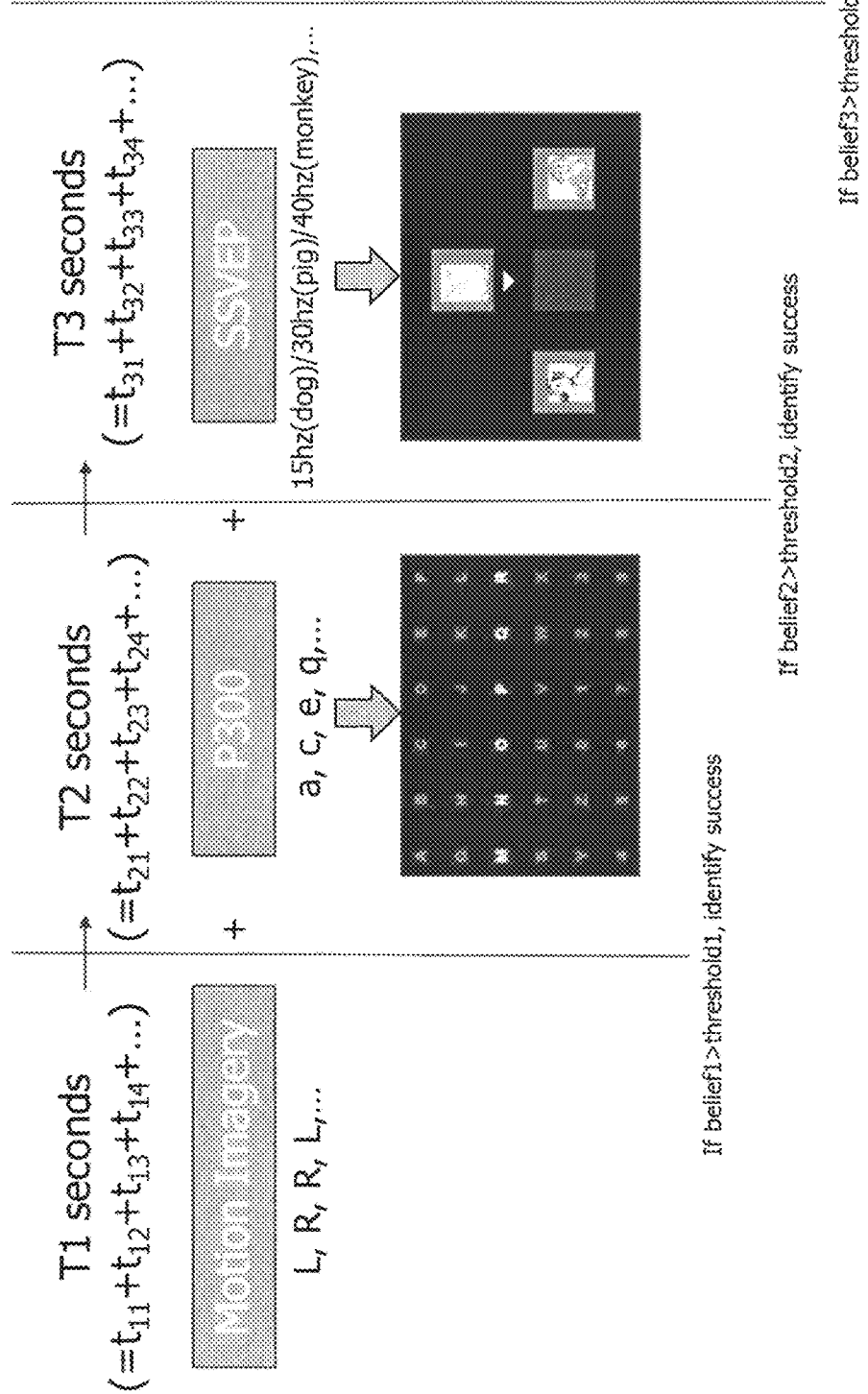
FIG. 6 exemplarily depicts a brain pattern generation according to an embodiment of the present invention.

Referring now to FIG. 1, in step 101, brain activity is decoded into brain pattern sequences, namely, a password. For example, as depicted in FIG. 6, the brain pattern sequences can include motion imagery, P300 wave, Steady-State Visual Evoked Potentials (SSVEP) tests over a time sequence. As depicted in FIG. 6, the motion imagery can be a first stage of a brain pattern sequence of which the brain activity to be decoded is L, R, R, L (e.g., left eye motion and right eye motion). In T1 seconds, a user model is used to determine if the user's brain activity satisfies the requirements. In a next time sequence (T2), event-related potential (ERP) such as P300 (P3) wave can be used to detect brain activity. For example, a user can be required to look at a canvas of the alphabet and numerals (or symbols and the like) and the brain activity to "look" at characters in a certain sequence (e.g., such as "a, c, e, q"). In a third time sequence (T3), SSVEP can be used to determine which at image out of a group of images that a user is looking by detecting visually-entrained brain waves. Each image at which the user is looking can be detected because they occur at specific frequencies. For example, if an image of a dog blinks at 15 hz, a pig at 30 hz, and a monkey at 40 hz, the EEG signals from the cortex can be used to look for any 15 hz, 30 hz, or 40 hz signal from the cortex. If a 15 hz signal is detected, then the user is looking at the dog. That is, each element of the password can be detected in a predefined time interval and elements of the password can be decoded from the same brain activities or also can be decoded from different activities.

In decoding the brain activity into the pattern sequences, if the belief that the users brain activity is greater than a threshold value, then part of the pattern sequence is identified as a success. That is, the "password" can be predetermined and the brain activity is decoded into a pattern sequence that matches the password to gain access. For example, if the user is generated a signal of 14 hz from their brain activity and the required hz for the dog image is 15 hz, then this may be within a threshold of the requirement for the passcode. The threshold can be set for each specific passcode to be satisfied by the brain pattern sequence.

It is noted that T1, T2, and T3 can be done in sequence of each individually based on the complexity required for the sequence. For example, a passcode for a safe in a bank can be required to have a time sequence passcode for ten sequences (e.g., T1 to T10) versus a login to pay a utility bill having one sequence (e.g., T1). Also, P300 may not be useable for some users and only motion imagery and SSVEP may give accurate results. Thus, P300 can be filtered out and never used in the pattern sequence.

Figure 2:
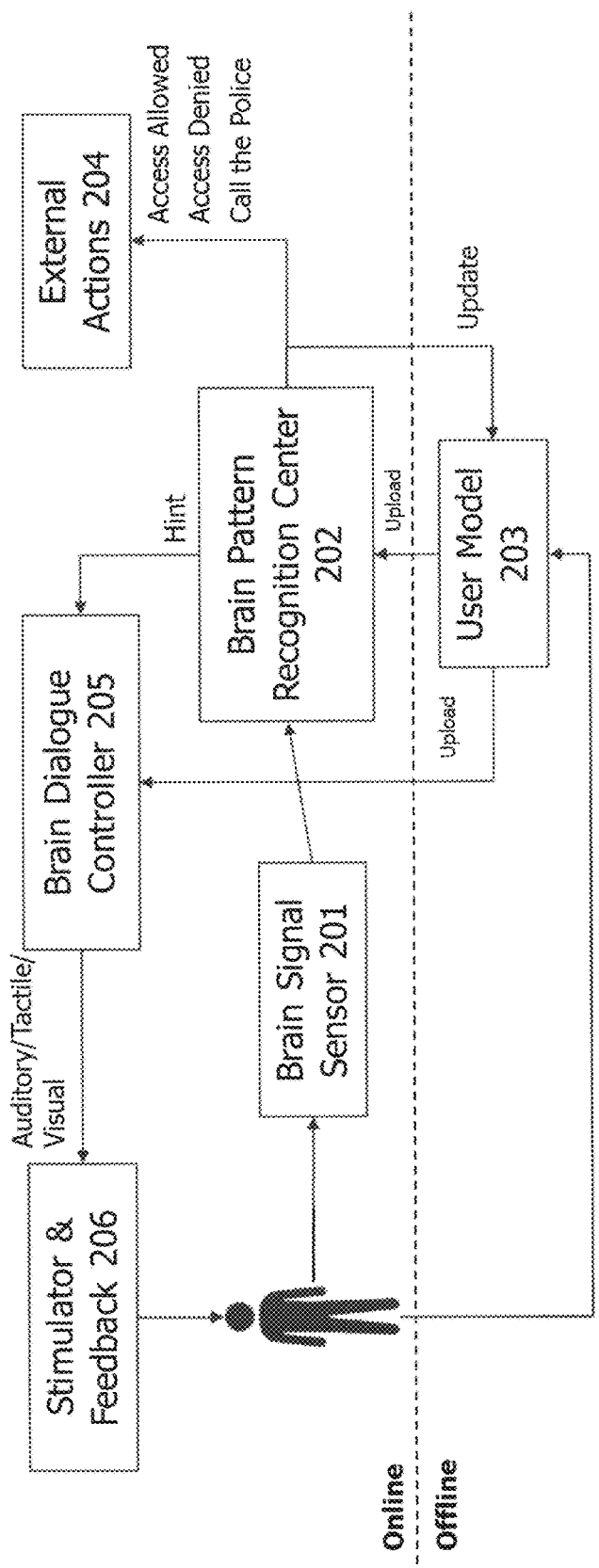
FIG. 2 exemplarily depicts an exemplary system 200 diagram according to an embodiment of the present invention.
Figure 3:
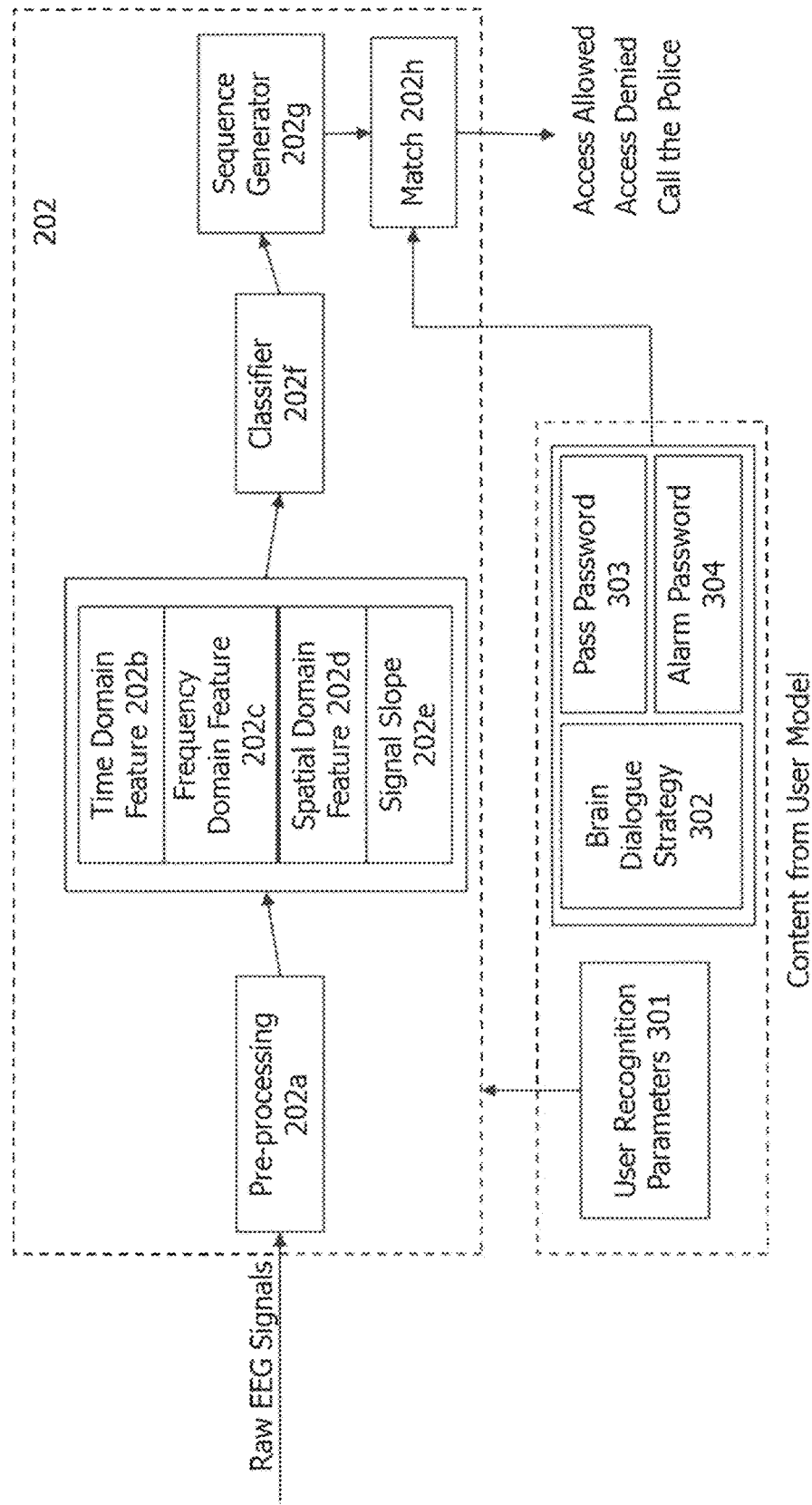
FIG. 3 exemplarily depicts a configuration of the brain pattern recognition center 202 according to an embodiment of the present invention.

As exemplarily depicted in FIGS. 2 and 3, the brain signal sensor 201 detects the brain activity of the user and sends the brain activity (i.e., raw electroencephalography (EEG) signals) to the brain pattern recognition center 202. The brain pattern recognition center includes pre-processing 202a of the raw EEG signals of which the time domain feature 202b (e.g., a time of the activity in the sequence T1, T2, T3), a frequency domain feature 202c of the raw EEG signals, a spatial domain feature 202d, and a signal slope 202e. The classifier 202f classifies the signal into the action performed by the user. For example, referring back to FIG. 6, the classifier classified if the user is looking at the dog (i.e., 15 hz) or the pig (i.e., 30 hz), at what time, and within a threshold time. Based on the classified user actions, the sequence generator 202g generates the sequence of the user actions (e.g., in T1, the user looked L, R, R, L, in T2, the user looked at a, c, e, q, and in T3 the user looked at a dog (e.g., 15 hz)). Based on the sequence, a match 202h is determined according to a password 303, alarm password 304, brain dialogue strategy 302, etc. to determine access to a system (e.g., determine external actions 204 such as allowing access, denying access, calling the police, etc.). In other words, if the password and the sequence match, then access is allowed. It is noted that the user recognition parameters 301 are individualized to each user (e.g., from the user model 203) to change the pre-processing 202a to be user specific. That is, each user's cortex values, for example, are different. Also, the user recognition parameters 301 can change a threshold for the match, the sequence, etc.

Figure 4:
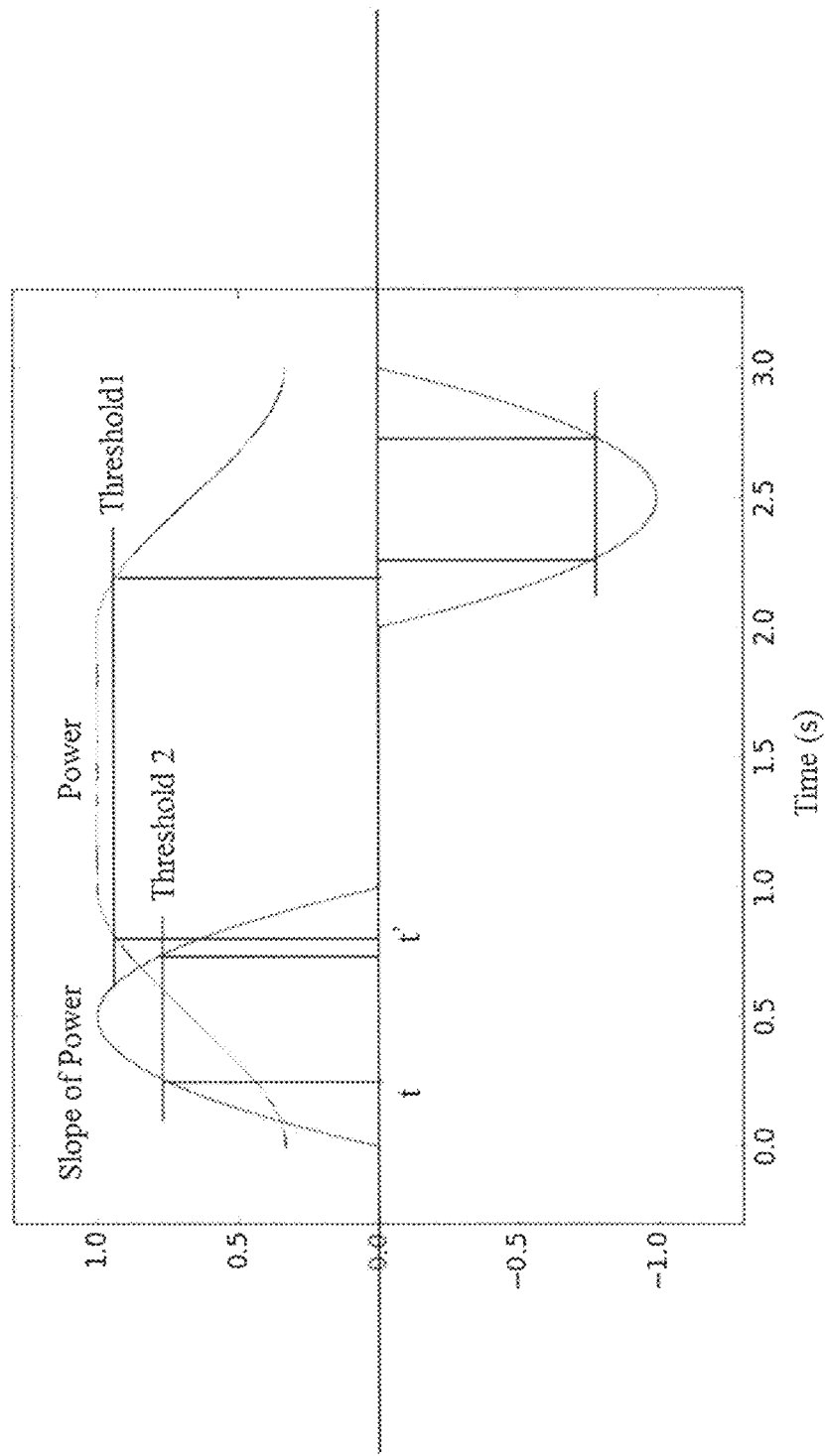
FIG. 4 exemplarily depicts a signal slope according to an embodiment of the present invention.
Figure 5:
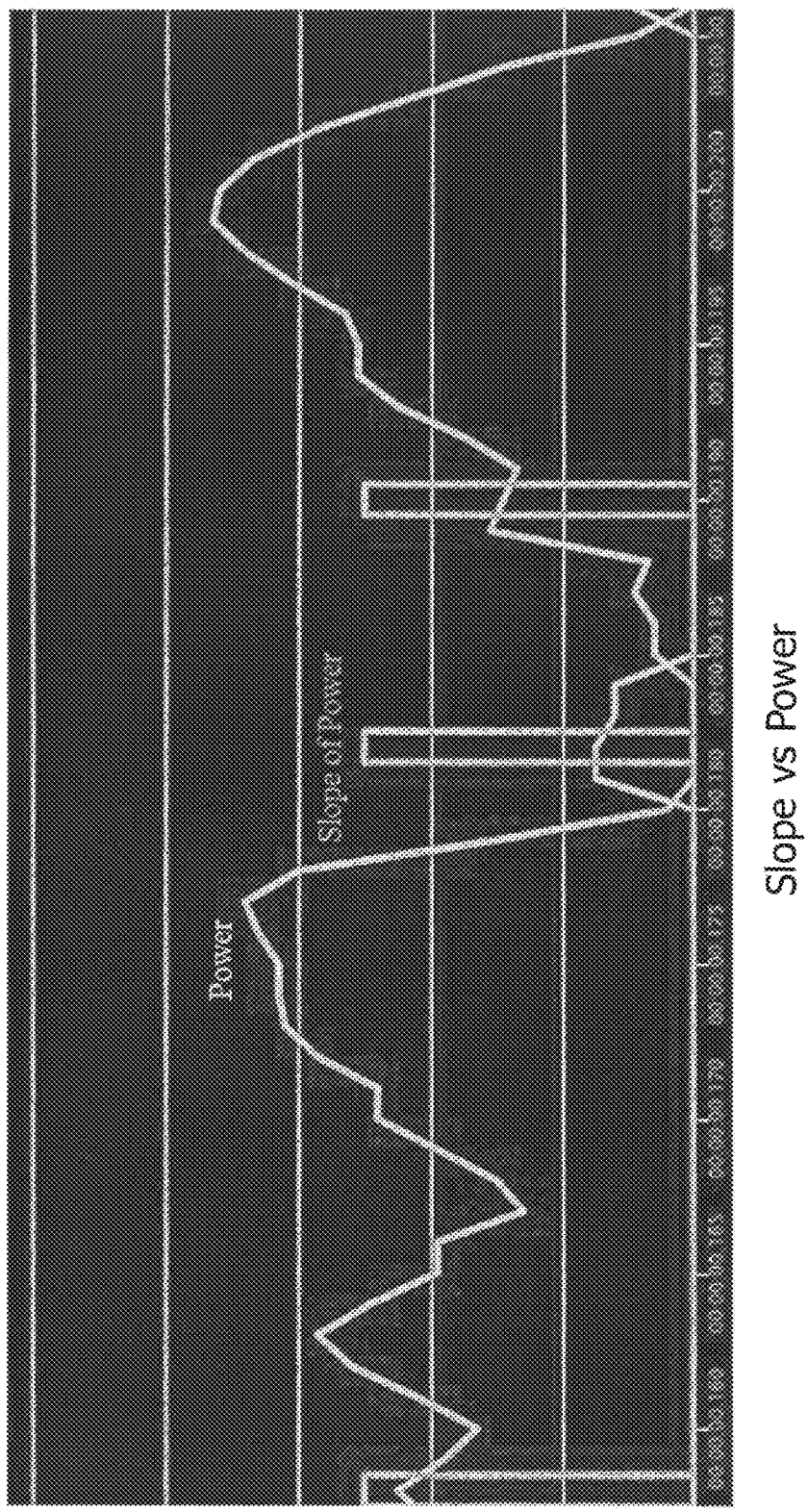
FIG. 5 exemplarily depicts a signal slope vs. power according to an embodiment of the present invention.

The signal slope 202e, as exemplarily depicted in FIG. 4, may be used instead of a power threshold of brain signal when determining the brain sequence. The slope threshold of the brain signal is utilized to determine the timing and duration of target brain patterns. With reference to FIGS. 4 and 5. As depicted in FIG. 4, the power of the original brain signal (e.g., SSVEP) is plotted, and its slope of power is also presented. In our invention, the signal slope is used to determine the timing and duration of brain patterns. In traditional methods based on signal power, "Threshold 1" determines the timing and duration of the valid brain signal. In our invention, "Threshold 2" in the left slope wave and right slope wave determines the timing and duration of the valid brain signal. Because the start time "t" of "Threshold 2" in the left slope wave is earlier than the start time "t'" of "Threshold 1", and the end time of "Threshold 2" in the right slope wave is later than the end time of "Threshold 1", the timing is earlier and duration is longer in our invention. Besides, the signal slope is an effective feature to feed the brain signal processing methods presented in FIG. 3.

A real use case is shown in FIG. 5, the original brain signal and its slope of power are both presented. The brain signal between each two slope power are assumed to be valid and used in our invention. By our invention, the timing is earlier and duration is longer when the brain signal is being processing.

Referring back to FIG. 1, in step 102, brain dialogue is applied to interact with the user in an invisible, customizable, and/or optimizable manner. For example, a noise can be emitted for the user to begin the brain activity from which to decode the sequence. Or, a different noise can be emitted to instruct the user if a correct passcode was entered or an error occurred with the passcode. Alternatively, any sense stimuli (e.g., touch, smell, sight, hearing, etc.) can be used as a "brain dialogue" to portray a message to the user that is invisible to other users. In other words, the brain dialogue is a message to the user that is only receivable by the user themselves. The brain dialogue controller 205 can control the output of the brain dialogue to the user.

In step 103, multi-module brain activities are combined to confirm the pattern sequence as a match against a predetermined pattern sequence. That is, for example, the brain activities of the SSVEP, P300, and Motion Imagery brain activities are combined into a single temporal sequence to confirm if the combined sequence matches a predetermined passcode or the like. In other words, the user input across multiple brain activity measuring techniques is combined to confirm a passcode. Thus, in step 103, a user will get authorization directly if recognition accuracy of the first brain activity is high enough. Otherwise, the user has to proceed to generate the next brain activity, the time domain feature, frequency domain feature, spatial domain feature, and signal slope of each brain activity are distilled and combined, and a new feature module (the slope of brain signal) is introduced to increase the accuracy and speed of recognition.

In step 104, an alarm module can be embedded into the pattern sequence that is triggered by specific brain activity. That is, in step 101, when the brain activity is being decoded into the brain pattern sequence, if the brain pattern sequence matches an alarm passcode, an alarm is triggered to call the police. For example, if the user ever has their brain activity decoded into "9, 1, 1" sequence, the police are called. In this manner, and since the user activity is invisible to other users, a user can call the police without others knowing if they are being forced to enter a passcode.

The user model 203 can be used to customize each feature of the pattern recognition to each specific user. In this manner, an adaptive user profile can be used to ensure the permanence, uniqueness and security of the inventive system.

Exemplary Aspects, Using a Cloud Computing Environment

Although this detailed description includes an exemplary embodiment of the present invention in a cloud computing environment, it is to be understood that implementation of the teachings recited herein are not limited to such a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 7, a schematic of an example of a cloud computing node is shown. Cloud computing node 10 is only one example of a suitable node and is not intended to suggest any limitation as to the scope of use or functionality of embodiments of the invention described herein. Regardless, cloud computing node 10 is capable of being implemented and/or performing any of the functionality set forth herein.

Although cloud computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing circuits that are linked through a communications network. In a distributed cloud computing environment, program modules may be located in both local and remote computer system storage media including memory storage circuits.

Referring now to FIG. 7, a computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further described below, memory 28 may include a computer program product storing one or program modules 42 comprising computer readable instructions configured to carry out one or more features of the present invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may be adapted for implementation in a networking environment. In some embodiments, program modules 42 are adapted to generally carry out one or more functions and/or methodologies of the present invention.

Computer system/server 12 may also communicate with one or more external devices 14 such as a keyboard, a pointing circuit, other peripherals, such as display 24, etc., and one or more components that facilitate interaction with computer system/server 12. Such communication can occur via Input/Output (I/O) interface 22, and/or any circuits (e.g., network card, modem, etc.) that enable computer system/server 12 to communicate with one or more other computing circuits. For example, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 8:
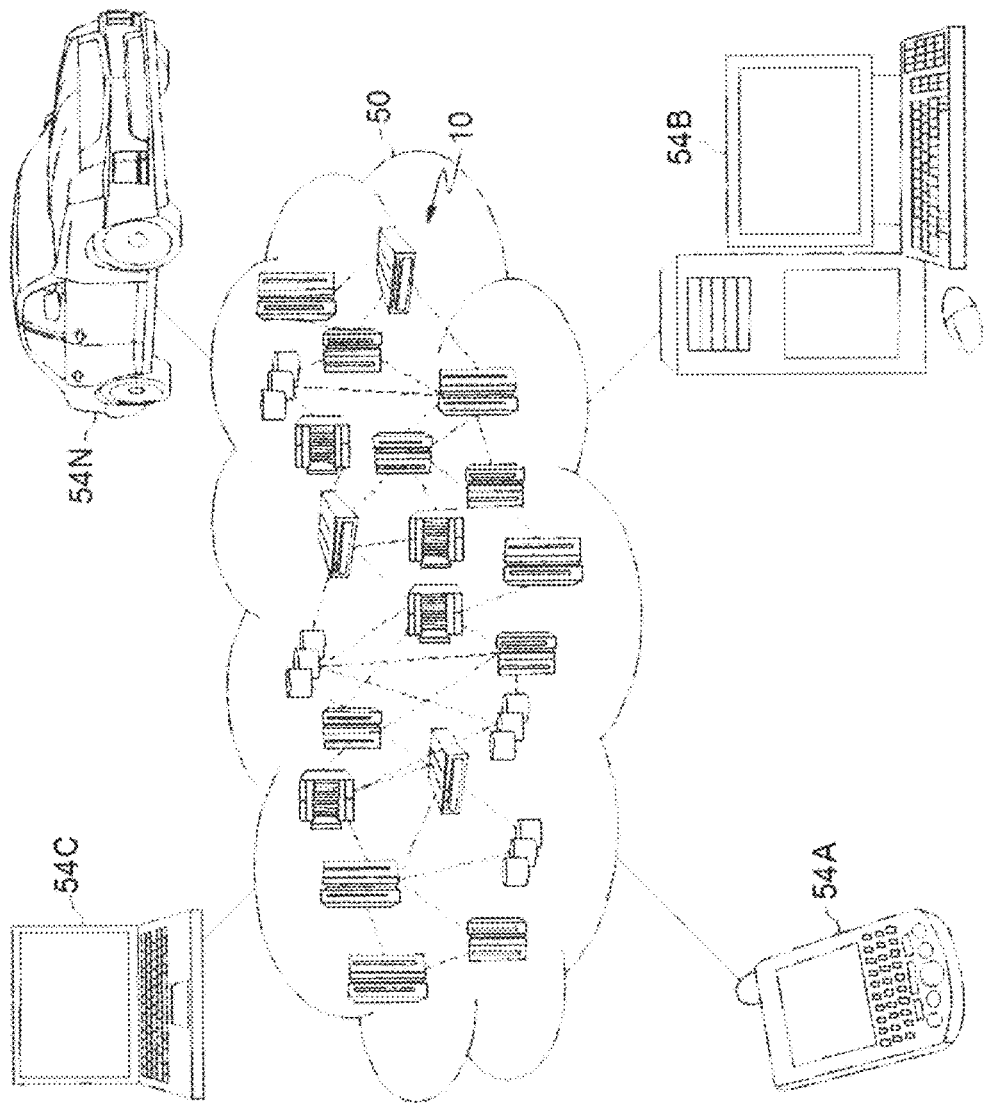
FIG. 8 depicts a cloud-computing environment 50 according to an embodiment of the present invention.

Referring now to FIG. 8, illustrative cloud computing environment 50 is depicted. As shown, cloud computing environment 50 comprises one or more cloud computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing circuit. It is understood that the types of computing circuits 54A-N shown in FIG. 8 are intended to be illustrative only and that computing nodes 10 and cloud computing environment 50 can communicate with any type of computerized circuit over any type of network and/or network addressable connection (e.g., using a web browser).

Figure 9:
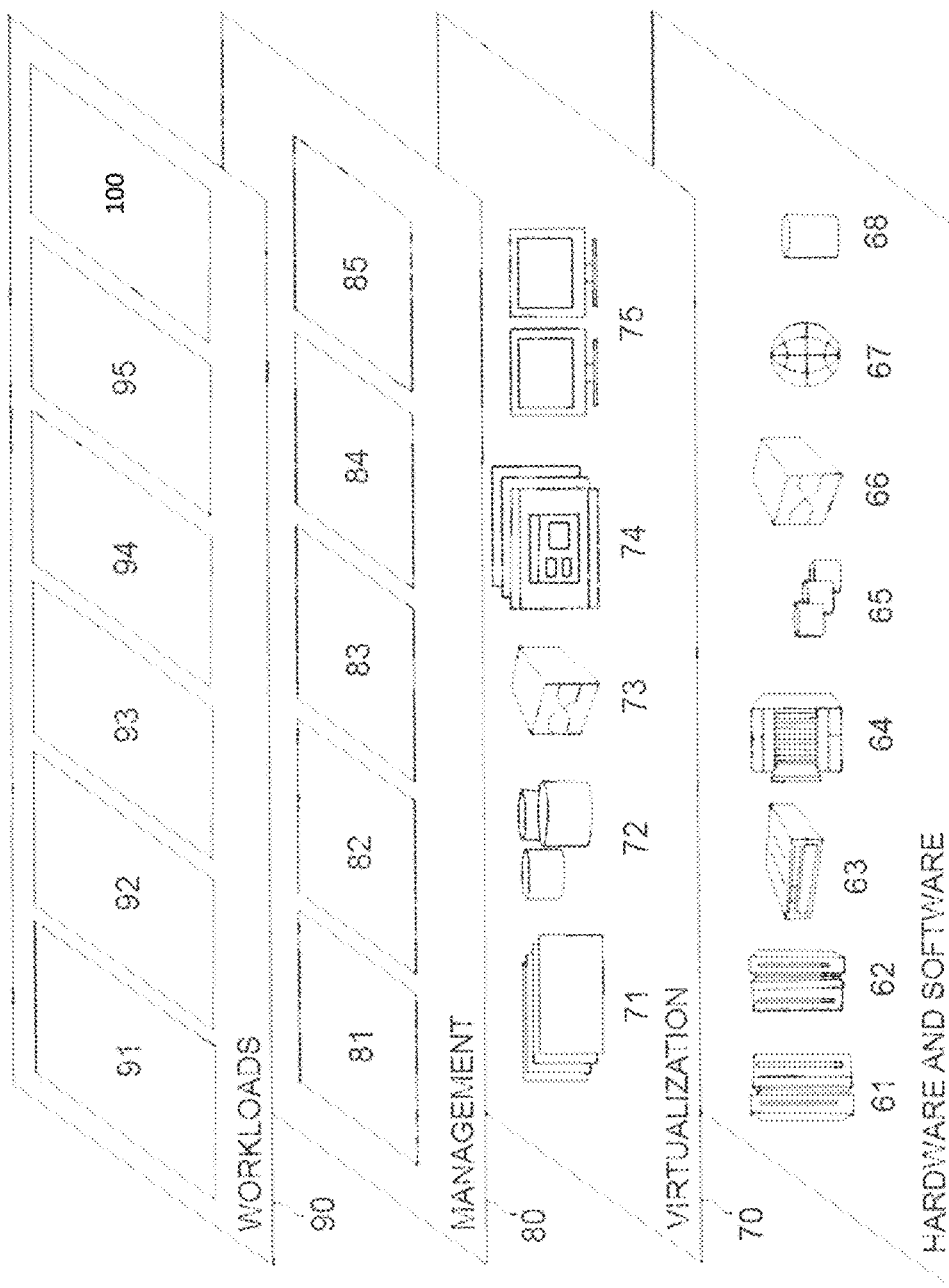
FIG. 9 depicts abstraction model layers according to an embodiment of the present invention.

Referring now to FIG. 9, an exemplary set of functional abstraction layers provided by cloud computing environment 50 (FIG. 8) is shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and authentication method 100 in accordance with the present invention.

The present invention may be a system, a method, and/or a computer program product at any possible technical detail level of integration. The computer program product may include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented authentication method, the method comprising:
    decoding brain activity into a brain pattern sequence as an entry for a password into a locked device;
    applying brain dialogue to interact with a user while the user is entering the brain pattern sequence;
    matching the brain pattern sequence with a predetermined password to allow access to a system; and
    embedding an alarm module which activates when the user is under a threat as determined by the brain pattern sequence matching a security password as the predetermined password,
    wherein a signal is sent to a third-party when the alarm module activates as a result of the threat, and
    wherein the decoding deducts the brain pattern sequence by analyzing a signal slope of a slope threshold of the brain activity to determine a timing and a duration of the brain activity.

2. The computer-implemented method of claim 1, wherein the brain activity is received via electroencephalography (EEG) of which is processed into a time domain feature, a frequency domain feature, a spatial domain feature, and a signal slope,
    wherein the brain activity is classified into user actions associated with the time domain feature, the frequency domain feature, the spatial domain feature, and the signal slope, and
    wherein the classified brain activity is matched with the predetermined password based on a threshold error compared to the time domain feature, the frequency domain feature, the spatial domain feature, and the signal slope of the brain activity.

3. The computer-implemented method of claim 1, wherein the brain dialogue comprises a sensory signal to the user that is invisible to other users.

4. The computer-implemented method of claim 1, wherein the brain pattern sequence comprises an element of a plurality of types of brain activity.

5. The computer-implemented method of claim 1, further comprising combining multi-mode brain activities to confirm the brain pattern sequence.

6. The computer-implemented method of claim 1, wherein the decoding the brain activity decodes the brain activity using at least one of motion imagery, P300, and Steady-State Visual Evoked Potentials (SSVEP).

7. The computer-implemented method of claim 1, wherein the brain pattern sequence comprises a multi-sequence brain pattern sequence of which a user will obtain authorization directly if a recognition accuracy of a first brain activity is greater than a predetermined threshold to proceed to a next sequence of the multi-sequence brain pattern sequence, and
    wherein a time domain feature, a frequency domain feature, a spatial domain feature, and a signal slope of each brain activity are distilled and combined.

8. The computer-implemented method of claim 1, wherein a signal slope is used to determine timing and a duration of brain patterns.

9. The computer-implemented method of claim 1, embodied in a cloud-computing environment.

10. A computer program product for authentication, the computer program product comprising a computer readable storage medium having program instructions embodied therewith, the program instructions executable by a computer to cause the computer to perform:
    decoding brain activity into a brain pattern sequence as an entry for a password into a locked device;
    applying brain dialogue to interact with a user while the user is entering the brain pattern sequence;
    matching the brain pattern sequence with a predetermined password to allow access to a system; and
    embedding an alarm module which activates when the user is under a threat as determined by the brain pattern sequence matching a security password as the predetermined password,
    wherein a signal is sent to a third-party when the alarm module activates as a result of the threat, and
    wherein the decoding deducts the brain pattern sequence by analyzing a signal slope of a sloe threshold the brain activity to determine a timing and a duration of the brain activity.

11. The computer program product of claim 10, wherein the brain activity is received via electroencephalography (EEG) of which is processed into a time domain feature, a frequency domain feature, a spatial domain feature, and a signal slope,
    wherein the brain activity is classified into user actions associated with the time domain feature, the frequency domain feature, the spatial domain feature, and the signal slope, and
    wherein the classified brain activity is matched with the predetermined password based on a threshold error compared to the time domain feature, the frequency domain feature, the spatial domain feature, and the signal slope of the brain activity.

12. The computer program product of claim 10, wherein the brain dialogue comprises a sensory signal to the user that is invisible to other users.

13. The computer program product of claim 10, wherein the brain pattern sequence comprises an element of a plurality of types of brain activity.

14. The computer program product of claim 10, further comprising combining multi-mode brain activities to confirm the brain pattern sequence.

15. The computer program product of claim 10, wherein the decoding the brain activity decodes the brain activity using at least one of motion imagery, P300, and Steady-State Visual Evoked Potentials (SSVEP).

16. The computer program product of claim 10, wherein the brain pattern sequence comprises a multi-sequence brain pattern sequence of which a user will obtain authorization directly if a recognition accuracy of a first brain activity is greater than a predetermined threshold to proceed to a next sequence of the multi-sequence brain pattern sequence, and
    wherein a time domain feature, a frequency domain feature, a spatial domain feature, and a signal slope of each brain activity are distilled and combined.

17. The computer program product of claim 10, wherein a signal slope is used to determine timing and a duration of brain patterns.

18. An authentication system, said system comprising:
    a processor; and
    a memory, the memory storing instructions to cause the processor to perform:

decoding brain activity into a brain pattern sequence as an entry for a password into a locked device;

applying brain dialogue to interact with a user while the user is entering the brain pattern sequence;

matching the brain pattern sequence with a predetermined password to allow access to a system; and embedding an alarm module which activates when the user is a under threat as determined by the brain pattern sequence matching a security password as the predetermined password, wherein a signal is sent to a third-party when the alarm module activates as a result of the threat, and wherein the decoding deducts the brain pattern sequence by analyzing a signal slope of a slope threshold of the brain activity to determine a timing and a duration of the brain activity.

* * * * *